(12) United States Patent
Delorme et al.

(10) Patent No.: US 8,337,391 B2
(45) Date of Patent: *Dec. 25, 2012

(54) SYSTEM FOR TREATING RECTOCELE IN A WOMAN

(75) Inventors: Emmanuel Delorme, Chalon sur Saone (FR); Georges Eglin, Beziers (FR); Jean-Marc Beraud, Saint-Etienne (FR)

(73) Assignee: Coloplast A/S, Humlebaek (DK)

( * ) Notice: Subject to any disclaimer, the term of this patent is extended or adjusted under 35 U.S.C. 154(b) by 669 days.

This patent is subject to a terminal disclaimer.

(21) Appl. No.: 12/509,492

(22) Filed: Jul. 27, 2009

(65) Prior Publication Data

US 2010/0030015 A1 Feb. 4, 2010

Related U.S. Application Data

(62) Division of application No. 10/811,158, filed on Mar. 29, 2004, now Pat. No. 7,588,598.

(60) Provisional application No. 60/458,007, filed on Mar. 28, 2003, provisional application No. 60/458,045, filed on Mar. 28, 2003.

(30) Foreign Application Priority Data

Mar. 28, 2003 (FR) ...................................... 03 03893
Mar. 28, 2003 (FR) ...................................... 03 03895

(51) Int. Cl.
*A61F 2/00* (2006.01)

(52) U.S. Cl. ......................................................... 600/37
(58) Field of Classification Search ..................... 600/29, 600/30, 37; 128/885; 606/151, 193; 623/11.11, 623/23.64–23.67

See application file for complete search history.

(56) References Cited

U.S. PATENT DOCUMENTS 7,494,495 B2 * 2/2009 Delorme et al. .............. 606/151

* cited by examiner

*Primary Examiner* — Christine Matthews
(74) *Attorney, Agent, or Firm* — Coloplast Corp., Coloplast A/S; Daniel G. Chapik; Nicholas R. Baumann (57) ABSTRACT

A system for treating rectocele in a woman includes an implant comprising a support body from which there extends at least to upper suspension stabilizers each disposed on either side of a sagittal plane on a longitudinal axis, the longitudinal axes forming between them an angle greater than 45°, and two lower suspension stabilizers disposed on either side of the sagittal plane; and an introduction device for inserting the implant in the woman, the introduction device shaped analogous to that of the implant and comprising a hollow body defining a cavity configured to receive the support body of the implant, tubular straps extending from the hollow body with each defining a cavity for receiving one of the suspension stabilizers of the implant, traction means extending from an end of each of the tubular straps, and a cut initiator provided on the hollow body.

13 Claims, 6 Drawing Sheets

SYSTEM FOR TREATING RECTOCELE IN A WOMAN

CROSS-REFERENCE TO RELATED APPLICATIONS

This application is a divisional of prior application U.S. patent application Ser. No. 10/811,158 filed on Mar. 29, 2004 now U.S. Pat. No. 7,588,598, which claimed the benefit of the filing date of U.S. Provisional Applications Nos. 60/458,007, filed Mar. 28, 2003, and 60/458,045, filed Mar. 28, 2003.

BACKGROUND

In general, the phenomena of prolapsus are the result of slackening of the tissues that suspend the genital or rectal organs, leading to troubles that require surgery.

Proposals have thus been made to attempt to reconstruct the natural system for suspending organs affected by the prolapsus, by putting non-resorbable sutures or reinforcing bands into place. Nevertheless, those techniques do not always give satisfaction, in particular because the surgery is invasive, leading to regions of the anatomy that are not concerned by the surgical repair being dissected in order to be able to stitch the non-resorbable sutures.

In an attempt to remedy those drawbacks, French patent application No. 2 785 521 proposes using an implant comprising a support body having two suspension cords suspending therefrom provided at their ends with anchor pieces for suturing to regions that have the reputation of being anatomically stable. That implant is then put into place by means of a laparoscope which enables the surgery to be less invasive.

Nevertheless, it has been found that such an implant does not guarantee effective suspension, in particular because of the stresses that are applied to the regions that have the reputation of being anatomically stable. In addition, in use, that type of implant does not present great stability in three dimensions.

SUMMARY

A system for treating rectocele in a woman includes an implant comprising a support body from which there extends at least two upper suspension stabilizers each disposed on either side of a sagittal plane on a longitudinal axis, the longitudinal axes forming between them an angle greater than 45°, and two lower suspension stabilizers disposed on either side of the sagittal plane; and an introduction device for inserting the implant in the woman, the introduction device shaped analogous to that of the implant and comprising a hollow body defining a cavity configured to receive the support body of the implant, tubular straps extending from the hollow body with each defining a cavity for receiving one of the suspension stabilizers of the implant, traction means extending from an end of each of the tubular straps, and a cut initiator provided on the hollow body.

Thus, the need has arisen firstly to have an implant providing better stability of implantation, and secondly a technique that enables good stability to be obtained, while minimizing the trauma to which the patient is subjected.

Thus, in order to achieve these objects, the invention provides an implant for treating rectocele, the implant presenting a structure that is thin and flexible and comprising a support body from which there extend at least two upper suspension stabilizers disposed on either side of the sagittal plane of the support body and two lower suspension stabilizers likewise disposed on either side of the sagittal plane.

According to the invention, the longitudinal axes of the upper stabilizers form between them an angle greater than 45°, and preferably but not strictly necessarily, an angle α lying in the range 100° to 180°, and more preferably in the range 115° to 170°. It should be observed that in a preferred embodiment, the sagittal plane constitutes an axis of symmetry of the implant and thus bisects the angle α.

Implementing upper suspension stabilizers presenting such a relative orientation makes it possible to place the stabilizers judiciously in the trans-sacrosciatic region so as to provide a good distribution of the forces applied by the support body to the anatomic anchor points of the stabilizers, while guaranteeing better orientation in three dimensions of the support body implanted in the patient.

According to a characteristic of the invention that is preferred but not strictly necessary, the upper and/or lower suspension stabilizers present a length greater than 100 millimeters (mm), and preferably greater than or equal to 120 mm. Such a length enables the suspension stabilizers to be extended well in their respective insertion regions so as to take advantage of friction between the suspension stabilizers or arms and the tissues through which they pass in order to hold the implant in place.

According to another characteristic of the invention, the longitudinal axes of the lower stabilizers form between them, preferably but not necessarily, an angle β that is not zero. Thus, it can be considered that the lower stabilizers are not parallel to each other. In preferred but not strictly necessary manner, the angle β is greater than 10° and preferably lies in the range 10° to 75°, or else in the range 100° to 180°, depending on the pathology that is to be treated.

According to yet another preferred but not strictly necessary characteristic of the invention, the support body presents a general shape that is substantially rectangular. In preferred but not strictly necessary manner, the support body then presents a length lying in the range 60 mm to 90 mm and a width lying in the range 40 mm to 60 mm.

In an embodiment of the invention, the upper stabilizers extend substantially from the upper corners of the support body and the lower stabilizers extend from the lower corners of the support body.

In another embodiment of the invention, the upper stabilizers extend substantially from the upper corners of the support body, while the lower stabilizers extend from the two long sides of the support body. Each of the lower stabilizers then preferably, but not necessarily, extends at a distance from the top edge of the support body lying in the range 60% to 87% of the length of the support body.

According to another characteristic of the invention, the lower stabilizers present respective enlarged regions where they join the support body of the implant. The invention also provides an operating technique for treating rectocele.

According to the invention, this technique consists in using an implant which comprises a support body from which there extend at least two upper suspension stabilizers disposed on either side of a sagittal plane, and at least two lower suspension stabilizers likewise disposed on either side of the sagittal plane. The technique consists firstly in placing the upper suspension stabilizers either in the corresponding trans gluteal region or in the corresponding sacrosciatic region, and also placing the lower stabilizers in the trans-pubo-rectal region.

In preferred manner, this technique is implemented in the context of so-called "mini-invasive" surgery using approaches that are close to the organs to be treated that are as small as possible, so as to reduce the time taken to perform the operation and reduce blood losses, thereby reducing the risk of erosion of the vagina by the prosthesis since the prosthesis does not face the incision exactly. It is thus possible to obtain postoperative periods that are short, with minimum discomfort for the patient. In addition, the simplicity of the technique makes it easy to reproduce and minimizes the training required to enable surgeons to master it.

In certain pathologies that are encountered, it can be found necessary to further increase the stability of the implant. Thus, according to a characteristic of the invention, the implant includes, in addition to the upper and lower pairs of suspension stabilizers, a middle pair of suspension stabilizers, each situated between an upper suspension stabilizer and a lower suspension stabilizer. The technique of treating rectocele implementing such an implant having six suspension stabilizers then provides for placing the implant in the body of the patient for treatment by positioning:

the upper suspension stabilizers through the sacrosciatic region;

the middle suspension stabilizers through the pubo-rectal region;

the lower suspension stabilizers through the perineal region; and the support body in the utero-sacral region.

The invention also provides an introduction device which can be used, although that is not absolutely essential in the meaning of the invention, for putting into place an implant as described above.

According to the invention, the introduction device comprises an introducer presenting a flexible structure of shape analogous to that of the implant and comprising:

a hollow body defining a cavity for receiving the support body of the implant;

tubular straps extending from the hollow body and each defining a cavity for receiving a suspension stabilizer of the implant;

traction means extending from the end of each of the straps of the introducer; and cut initiator means at least for the hollow body of the introducer.

According to a characteristic of the invention, for each tubular strap, the traction means comprise a semirigid needle.

According to the invention, the cut initiator means may be implemented in any suitable manner, such as, for example, in the form of a line of weakness suitable for being torn when traction is applied to two opposite tubular straps of the introducer.

According to a characteristic of the invention that is preferred but not strictly necessary, the cut initiator means comprise at least one opening for passing a cutting tool. In preferred manner, the introducer body has a series of openings situated firstly close to a line corresponding to the sagittal plane of the implant and secondly between the tubular stabilizers.

According to another characteristic of the invention, the introduction device includes an implant in accordance with the invention placed in the hollow body cavity and in the tubular straps of the introducer. In preferred but not strictly necessary manner, the implant is loose inside the introducer.

In order to make the surgeon's work easier, according to another characteristic of the invention, the introduction device also includes at least one ancillary device comprising an elongate perforator guide or trocar having one end for insertion into the body of the patient and having its opposite end provided with a handle.

According to a characteristic of the invention, the perforator guide presents a shape that is arcuate in a plane. In preferred but not strictly necessary manner, the arcuate portion of the perforator extends over an angular sector of greater than 140°, and preferably but not necessarily less than 180°, preferably lying in the range 150° to 170°. In preferred manner, the arcuate portion of the perforator guide then presents a radius of curvature lying in the range 30 mm to 60 mm, and preferably for that portion of the perforator guide that extends from the handle to the end that is for insertion into the body of the patient in the range 40 mm to 50 mm, the end portion of the perforator then presenting a varying radius of curvature.

In another embodiment, the distal end of the perforator guide, i.e. its end remote from the handle, presents a shape that is helical. In preferred manner, the perforator guide then presents the shape of a portion of a helical turn extending over an angle lying in the range 180° to 360°, and preferably lying in the range 255° to 270°. Likewise, in preferred manner, the turn of the perforator guide presents a radius of curvature lying in the range 20 mm to 40 mm, and pitch lying in the range 15 mm to 25 mm.

According to another characteristic of the invention, in order to reduce the trauma suffered by the body of the patient during introduction of the implant, the introduction device further comprises a tubular sleeve of shape complementary to that of the perforator guide. The tubular sleeve is then intended to be engaged on the perforator guide and to remain in the body of the patient after the perforator guide has been withdrawn so as to define a tunnel for passing the traction means of the introducer. The tubular sleeve is subsequently withdrawn, after the traction means have been passed while withdrawing the introducer.

According to the invention, the tubular sleeve may be made of any flexible and biocompatible material, such as, for example and not exclusively, polyvinyl chloride (PVC).

BRIEF DESCRIPTION OF THE DRAWINGS

Various other characteristics of the invention appear from the following description made with reference to the accompanying drawings which show various embodiments of an implant of the invention, together with introducing devices for making said implant easier to put into place.

Furthermore, it should be observed that the various characteristics of the invention as described above and below can be combined with one another in a variety of ways depending on the pathology to be treated.

DETAILED DESCRIPTION OF THE INVENTION

Figure 1:
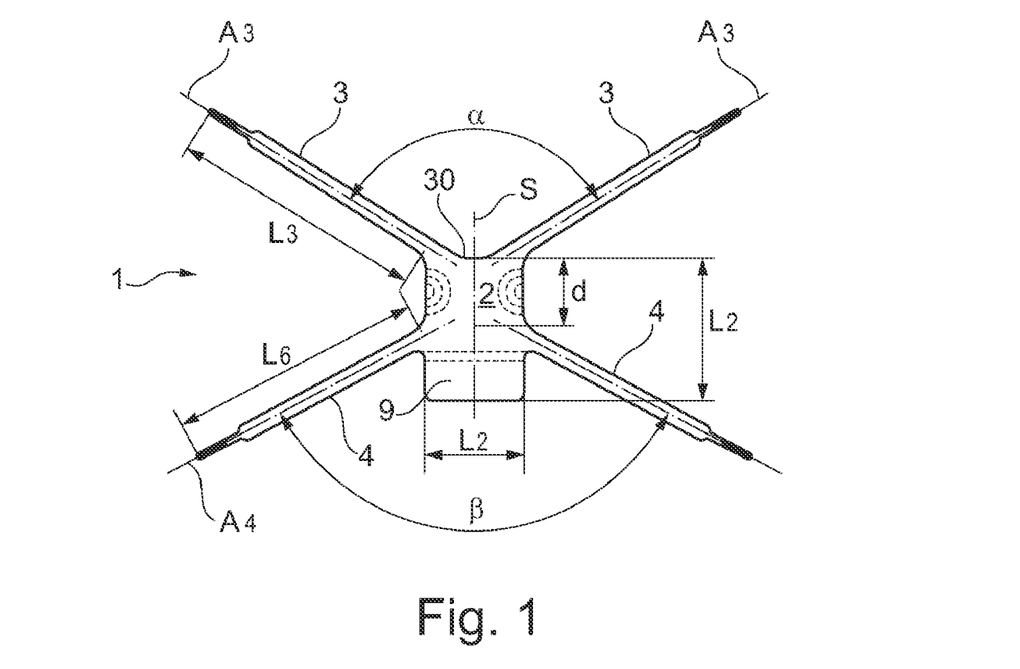
FIG. 1 is an elevation view shown flat of an implant of the invention for the treatment of rectocele.

The invention provides an implant more particularly designed to treat rectocele and given overall reference 1 in FIG. 1. The implant 1 presents a structure that is thin and flexible and is made of a suitable biocompatible material, such as for example: an optionally woven synthetic material or indeed a knitted material based on polypropylene or polyester fibers. Such a synthetic material can optionally be coated in substances that encourage cell growth. Similarly, the implant of the invention could be made of natural materials, such as "fascia latta" or indeed any resorbable biological or synthetic material.

In accordance with the invention, the implant 1 comprises a support body 2 from which there extend two upper suspension stabilizers 3 disposed on either side of a sagittal plane S. The implant also comprises two lower suspension stabilizers 4 also disposed on either side of the sagittal plane S. These stabilizers act by the striction implemented by muscle masses.

In the example shown, the support body 2 is substantially rectangular in shape, although that shape cannot be considered as being strictly necessary in the meaning of the invention, and each of the upper suspension stabilizers 3 extends from an upper corner of the body 2. Each of the lower suspension stabilizers 4 extends from a side of the rectangularly-shaped support body 2.

Thus, given the disposition of the lower suspension stabilizers 4, the body 2 of the implant 1 has a kind of small lower apron 9.

In the example shown, the lower suspension stabilizers 4 begin on a side of the support body 2 at a distance d from the upper edge 30 of the support body 2, which distance is preferably, but not strictly necessarily, in the range 60% to 87% of the length $L_2$ of the support body.

Preferably, the support body 2 is selected to present a length $L_2$ lying in the range 60 mm to 90 mm and a width $L_2$ lying in the range 40 mm to 60 mm.

According to a preferred characteristic of the invention, the longitudinal axes $A_3$ of the upper stabilizers 3 form an angle α that is greater than 45°, and preferably lying in the range 100° to 180°, lying in more particularly preferred manner in the range 115° to 170°.

Furthermore, in the embodiment shown in FIG. 1, the axes $A_4$ of the lower suspension stabilizers 4 form a non-zero angle β between each other, which angle is preferably greater than 10°, and in the embodiment shown the angle β lies in the range 100° to 180°. It should be observed that in preferred manner the sagittal plane S corresponds to a plane of symmetry of the implant 1 and therefore bisects the angles α and β.

In order to make it easier to put the suspension stabilizers into place in their corresponding insertion regions, while providing a good area of friction with the tissue through which they pass, the upper and lower suspension stabilizers 3 and 4 are of respective lengths $L_3$, $L_4$ measured between the distal end of each suspension stabilizer and the support body 2 that are preferably although not necessarily greater than 100 mm, and in more particularly preferred manner greater than 120 mm. The suspension stabilizers may also be of width that preferably but not exclusively lies in the range 5 mm to 15 mm, being equal to about ten millimeters, for example.

The implant 1 as described is for putting into place at the recto-vaginal septum of a patient. For this purpose, in order to minimize dissection of this region and the resulting trauma, the invention provides the surgeon performing the treatment with the option of using one or more elongate perforator guides 10 such as those shown in greater detail in FIGS. 2 and 3 to 5.

In general, such a perforator guide 10 comprises an elongate body or prong 11 having one end 12 for insertion into the body of a patient to be treated and whose other end 13 is provided with a handle 14. It should be understood that the introduction end 12 is preferably constituted by a blunt tip, i.e. a tip that is not traumatic and which is not suitable for injuring or cutting the tissue into which it is to be inserted.

Figure 2:
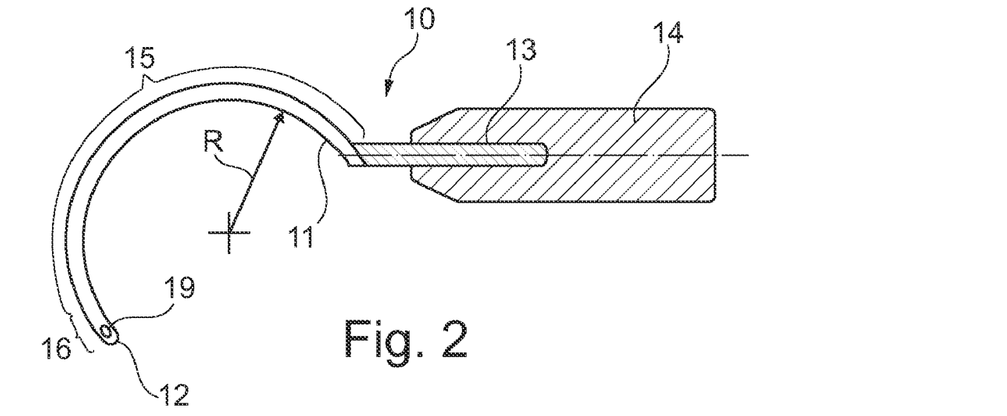
FIG. 2 is a partially cut-away elevation view of a perforator guide suitable for being used for putting into place an implant of the invention presenting an arcuate shape.

In an embodiment shown in FIG. 2, the perforator guide 10 is of a shape that is arcuate in a plane. This planar arcuate shape is more particularly suitable for putting suspension stabilizers into place in the transperineal and transgluteal regions. In preferred, but not strictly necessary manner, the arcuate portion of the perforator guide then presents a radius of curvature R lying in the range 30 mm to 60 mm, and preferably for the portion 15 of the perforator guide 10 that extends from the handle 14 to the end 12, lying in the range 40 mm to 50 mm, the end portion 16 of the perforator guide 10 then presenting varying radius of curvature.

Figure 3:
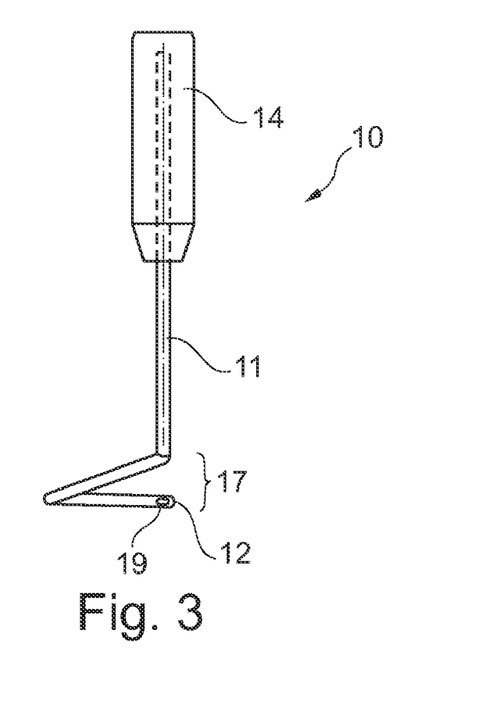
FIG. 3 is an elevation view of another embodiment of a perforator guide of the invention, presenting an introduction end of helical shape.
Figure 4:
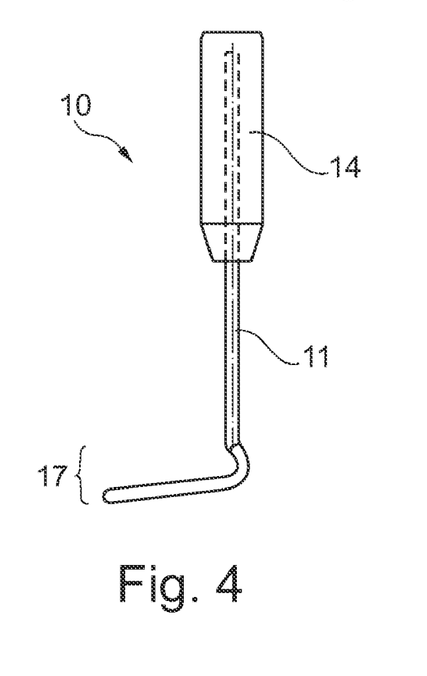
FIG. 4 is a left-hand view of the FIG. 3 perforator guide.
Figure 5:
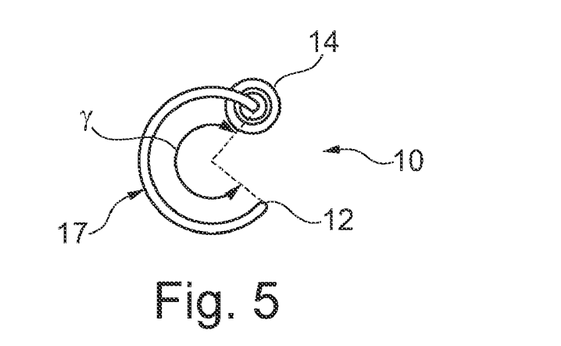
FIG. 5 is a view from beneath of the perforator shown in FIG. 3.

In another embodiment of the perforator guide 10 as shown in FIGS. 3 to 5, the elongate body 11 of the guide 10 presents a helically-shaped end 17 likewise adapted for putting suspension stabilizers into place in the upper or lower regions of closed holes. In preferred manner, the distal end 17 of the perforator guide is then in the form of a portion of a helical turn extending over an angle γ lying in the range 180° to 360°, and preferably in the range 255° to 270°. Similarly, and in preferred manner, the turn 17 of the perforator guide presents a radius of curvature lying in the range 20 mm to 40 mm, with a pitch lying in the range 15 mm to 25 mm.

The implant 1 of the invention is preferably disposed in such a manner as to present no residual tension after it has been put into place, at least in some of its suspension stabilizers. In order to make this surgery easier to perform, the invention proposes in a variant to implement an introducer shown more particularly in FIG. 6 and given overall reference 20.

This introducer is of flexible structure and of shape analogous to that of the implant. The introducer 20 is preferably made of a biocompatible polymer material taken from the family of plastics materials having a low coefficient of friction, such as, for example, polyethylene. The introducer 20 then comprises a hollow body 21 defining a cavity for receiving the body 2 of the implant 1. The introducer 20 also comprises tubular straps 22 which extend from the hollow body 21 and which define respective cavities for receiving respective suspension stabilizers 3 and 4 of the implant 1. Each tubular strap 22 then presents traction means extending from the free end of the corresponding strap 22. The traction means 23 may be made in any suitable manner, such as for example systems for hooking the ends of the straps 22 onto a perforator guide 10. In the example shown in FIG. 6, for each strap 22, the traction means comprise a flexible or semirigid needle having a nontraumatic or blunt end. Such a needle can be made out of the same material as the material constituting the introducer 20, or more generally out of a material selected from synthetic polymers that preferably present a low coefficient of friction.

Finally, the introducer 20 includes cut initiator means 24 whose function is described below for use in cutting at least the hollow body 21 of the introducer 20. The cut initiator means 24 may be implemented in any appropriate manner, and in the example shown they comprise a series of six openings 24 made in the periphery of the hollow body 21, between each of the tubular straps 22, so as to pass a cutting tool to cut through the hollow body 21 along lines 25 that are represented by chain-dotted lines in FIG. 6.

Figure 6:
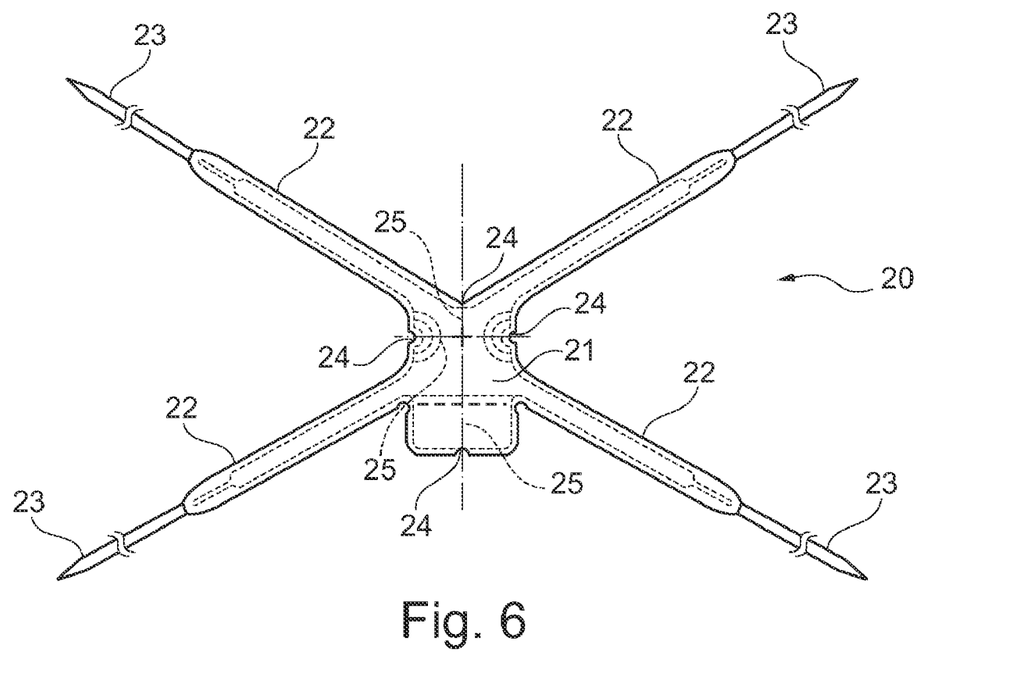
FIG. 6 is a view of an introducer of the invention enabling the implant shown in FIG. 1 to be put into place.

The implant 1 is placed inside the hollow body 21 and the tubular straps 22, preferably being loose inside them so that the forces exerted on the introducer 20 are not transmitted to the implant 1 itself.

Rectocele surgery, using an implant 1 and perforator guide 10 as described above, is performed as follows.

The patient for treatment is initially anesthetized either generally, regionally, or indeed locally, depending on the preferences of the surgeon and on the state of health of the patient. The operating position of the patient on the operating table is the usual position for vaginal surgery, i.e. the patient's buttocks are slightly beyond the operating table and the thighs are flexed moderately towards the abdomen.

Initially a rectal wick is put into place and an ischemia-inducing injection is performed.

Thereafter, the region that is to receive the support body 2 of the implant 1 is dissected. Traction is exerted on the cervix of the uterus in order to expose the posterior fornix. A vaginal incision is made in the posterior portion of the cervix across the cervical slope of the fornix that has been thoroughly exposed by the traction. This incision may be referred to as being horizontal and retrocervical. The edge of the lower vaginal section made in this way is held in full, e.g. by means of three Alis clamps which are pulled downwards, exposing the rectovaginal plane.

Rectovaginal separation is performed progressively, thereby releasing the posterior vaginal wall. This separation is stopped downwards and in the middle over the anal cap. Separation is continued laterally in the dissection plane and into contact with the levator muscle going upwards through the pubo-coccygeal bundle and then the ilio-coccygeal bundle to reach the coccygeal muscle and the sacrosciatic ligament. This dissection is performed carefully pushing back the perirectal fat and the rectum inwards. It should be observed that there is then no structure to be sectioned and it suffices to push back the perirectal fat inwards while remaining in contact with the muscle floor. The most practical method for performing this dissection consists in using a finger, a compress, and a set of narrow and long vaginal valves (modified Breisky valves) insofar as they enable view of the space to be opened progressively under control without excessive enlargement, thus enabling a finger to be inserted to perform the dissection.

Once this dissection work has been performed, it is possible to proceed with introduction of the implant 1, either bare or else encapsulated in the introducer 20. Initially a first upper suspension stabilizer 3 is put into place. For this purpose, an arcuate perforator guide 10 selected by the surgeon and as described above with reference to FIGS. 2 and 3 to 5 can be used. The perforator guide 10 is then taken through the patient's buttock by a point incision situated about 15 mm behind the midpoint of the line extending from the anus to the ischium. A finger slid into the lateral separation in contact with the sacroiliac ligament as previously prepared then receives the tip of the perforator guide so as to lead it into the lower vaginal incision. A traction element 23 of the introducer 20 in association with the upper suspension stabilizer 3 is fixed in an eye 19 formed by the end of the perforator guide 10 which is then withdrawn in the opposite direction so as to take with it the tubular strap 22 of the introducer 20 together with the upper suspension stabilizer or arm 3 that it contains. The strap being pulled then passes through the sacroiliac ligament. It should be observed that in the absence of the introducer 20, the distal end of the upper suspension stabilizer is fixed directly to the perforator guide 10 so as to enable it to be pulled.

The same action is performed to put the second upper stabilizer 3 into place. Once the upper stabilizers 3 have been put into place in this way to provide transgluteal 20 suspension, they are put in a standby position on clamps.

The lower suspension stabilizers 4 are then passed through the pubo-rectal muscle on either side of the anal canal and are taken to the outside through the same orifice in the buttocks as the upper stabilizers 3.

Once all four suspension stabilizers 3, 4 have been engaged, the introducer 20 is cut away so as to release the implant 1. The various elements making up the introducer 20 are withdrawn by exerting traction in pairs on opposite tubular straps 22, thereby enabling the implant 1 to be put into place without applying any other stress thereto, so that the implant is in a state that can be referred to as relaxed.

The support body 2 of the implant 1 is then fixed to the uterosacral ligaments and the apron 9 is fixed onto the lower face of the cervix of the uterus, using one or more, and preferably three stitches of resorbable suture.

The posterior vaginal incision is then sutured with resorbable material and traction is exerted on the upper suspension stabilizers 3 passing through the sacrosciatic region so as to raise the fornix of the vagina into the proper place. Any excess length of upper or lower suspension stabilizer 3 or 4 can then be sectioned and the orifices in the buttocks closed by means of stitches made of resorbable suture material.

At the end of surgery, a vaginal wick is put into place together with a bladder probe, which are removed forty-eight hours after surgery. Post-mictional residues are then measured by probing in order to ensure that the bladder is emptied in satisfactory manner and the patient can be allowed to leave.

The surgery for treating rectocele lasts for about one hour and it is appropriate for hospitalization to last on average for four days. The patient's activity will be restricted for one month and it is appropriate to avoid taking a bath throughout that time. Finally, it is appropriate to provide for a period of sexual abstinence of six weeks following the operation.

The technique as proposed above thus makes it possible to treat the pathology on its own, i.e. disequilibrium of the static portions within the pelvis region and thus to restore anatomy that is as normal as possible while conserving the individual's body image. This technique makes it possible, advantageously, to conserve organs that are healthy or that are not having any unfavorable influence on the static portions within the pelvis region. Cancer will have been discounted by pre-operative checks and after the surgery it will be possible to provide reliable gynecological monitoring.

The risk of pelvic genital cancer is very small, and in any event the treatment proposed by the invention does not complicate subsequent access to the genital organs or to the rectal region.

Figure 7:
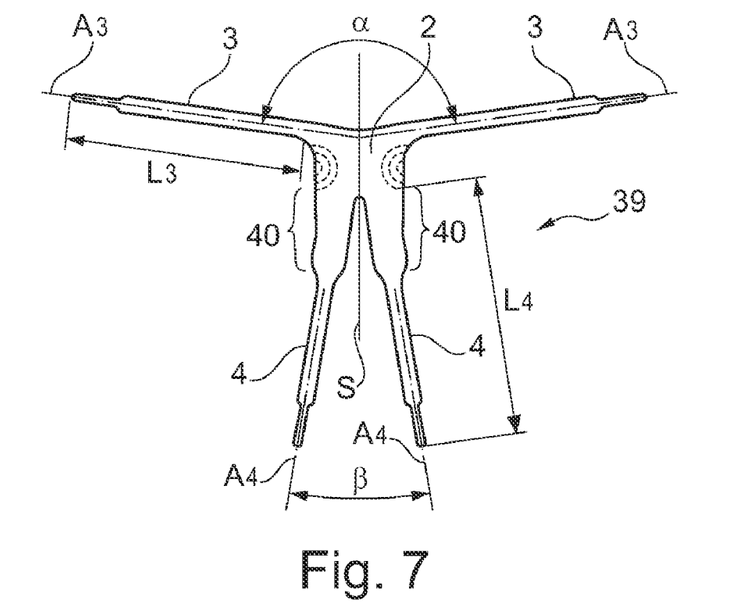
FIG. 7 is a view analogous to FIG. 1 showing a variant embodiment of the implant of the invention.

With the embodiment of the implant shown in FIG. 1, the lower suspension stabilizers 4 extend from the sides of the support body, however that is not strictly necessary for implementing an implant of the invention. Thus, FIG. 7 shows an implant 39 in accordance with the invention in which all four suspension stabilizers, the upper two stabilizers 3 and the lower two stabilizers 4 extend from respective corners of the support body 2.

In this embodiment, the axes $A_3$ of the upper suspension stabilizers form an angle $\alpha$ presenting the same characteristics as those of the above-described implant 1, whereas the axes $A_4$ of the lower suspension stabilizers 4 form an angle $\beta$ that preferably, but not exclusively, lies in the range 10° to 75°.

Figure 8:
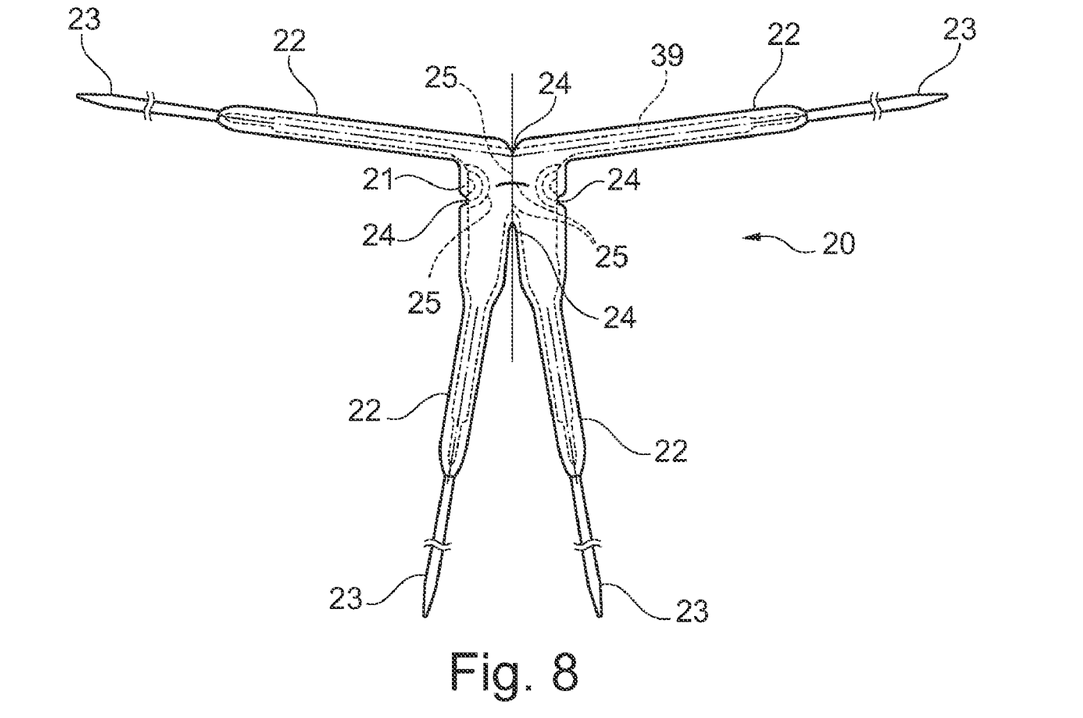
FIG. 8 is a view analogous to FIG. 6 showing an introducer for putting the FIG. 7 implant into place.
Figure 9:
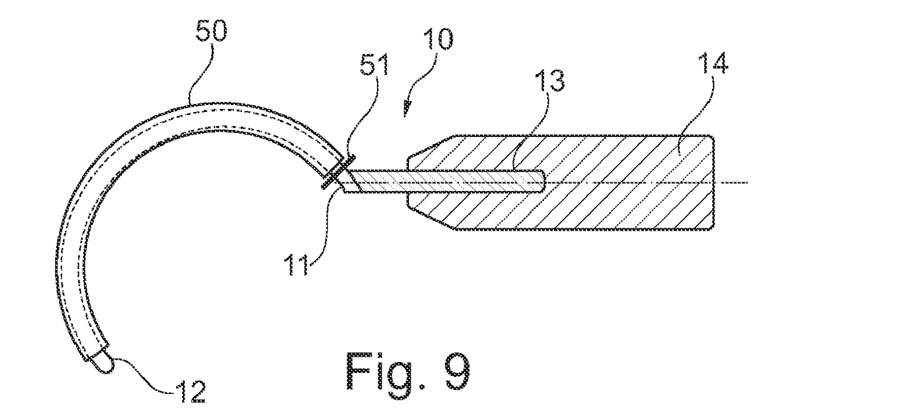
FIGS. 9 to 12 are views analogous to FIGS. 2 to 3 showing variant embodiments of perforator guides for putting into place an implant in accordance with the invention.
Figure 10:
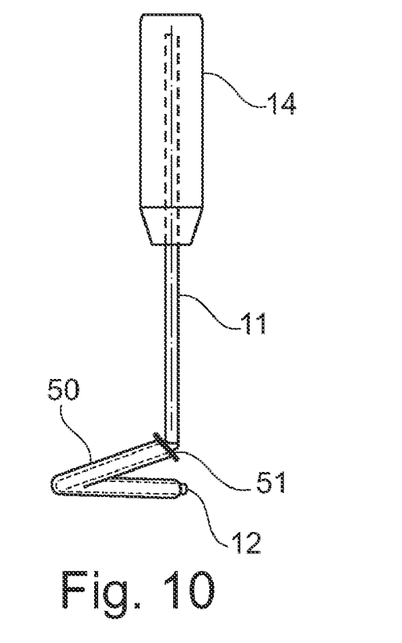
Figure 11:
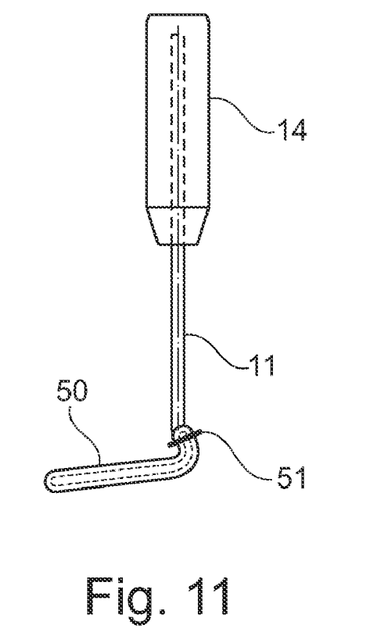
Figure 12:
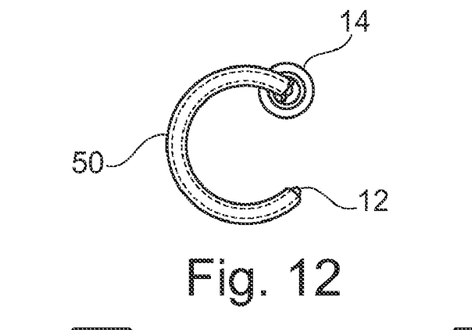

Furthermore, the lower suspension stabilizers 4 are of enlarged shape at their proximal ends 40 where they leave the support body 2, thereby forming a pre-rectal suspension FIG. 8 shows an example of an introducer 20 that is more particularly adapted to the conformation of the implant 39.

The operation for treating rectocele by means of the implant 39 is performed in the same manner as that described above when it comes to dissection of the rectovaginal region that receives the support body 2 and putting the lower and upper suspension stabilizers 3 and 4 into place.

The enlarged portions 40 of the lower suspension stabilizers 4 can be fixed by resorbable suture stitches to the levator muscles in the pubo-rectal region.

Similarly, it can be envisaged that the lower suspension stabilizers 4 are passed through the perineum. This positioning of the pre-rectal hammock in a transperineal configuration advantageously strengthens the perineal plane with the transgluteal upper suspension so as to reinforce the descending perinea.

In the treatment and operation described above, the introduction device used comprises simple perforator guides 10. Nevertheless, in order to minimize trauma by abrasion of the regions of tissue through which it passes, it can be envisaged that an ancillary device is implemented associating the perforator guide 10 with a flexible sleeve 50 of shape complementary to that of the guide 10, as shown in FIGS. 9 and 10 to 13. The sleeve 50 is engaged on the perforator guide 10 which then presents an abutment or guard 51 against which the sleeve 50 comes to bear during insertion of the perforator guide 10 into the body of the patient. The sleeve 50 is left in place in the body of the patient after the perforator guide 10 has been removed and prior to putting the implant 1, 39 into place. The sleeve thus enables a channel to be created for passing a traction element 23 of the introducer 20 in which a tubular strap 23 and the associated suspension arm or stabilizer 3 or 4 is passed or else a suspension stabilizer or arm on its own 3 or 4 can be moved by sliding so as to adjust the position of the implant 1, 39 without abrading the tissues through which it passes. A sleeve 50 is then used for putting each suspension stabilizer 3 or 4 into place. The sleeves 50 are subsequently withdrawn together with the tubular straps 23 surrounding the suspension stabilizers of the implant or when the implant is put into place bare and after adjusting the position of the implant.

Thus, the use of sleeves 50 avoids phenomena of acute inflammation and reduces the trauma to tissue insofar as the implantation sites are constituted by highly specialized muscle tissue that has lost a large fraction of its ability to regenerate and to heal rapidly.

In the implant embodiments described above, the upper and lower suspension stabilizers 3 and 4 extend from the body of the implant in diverging manner, thereby giving the implant a shape that could be referred to as "star-shaped". Nevertheless, this star shape is not strictly necessary when making an implant of the invention, and for certain pathological conditions it can be necessary to have an implant in which the suspension stabilizers do not diverge, but on the contrary have free ends on the upper and lower stabilizers 3 and 4 that are directed downwards. Under such circumstances, the longitudinal axes $A_3$ of the upper stabilizers form an angle $\alpha$ that is greater than 180°, and preferably greater than 200°.

Figure 13:
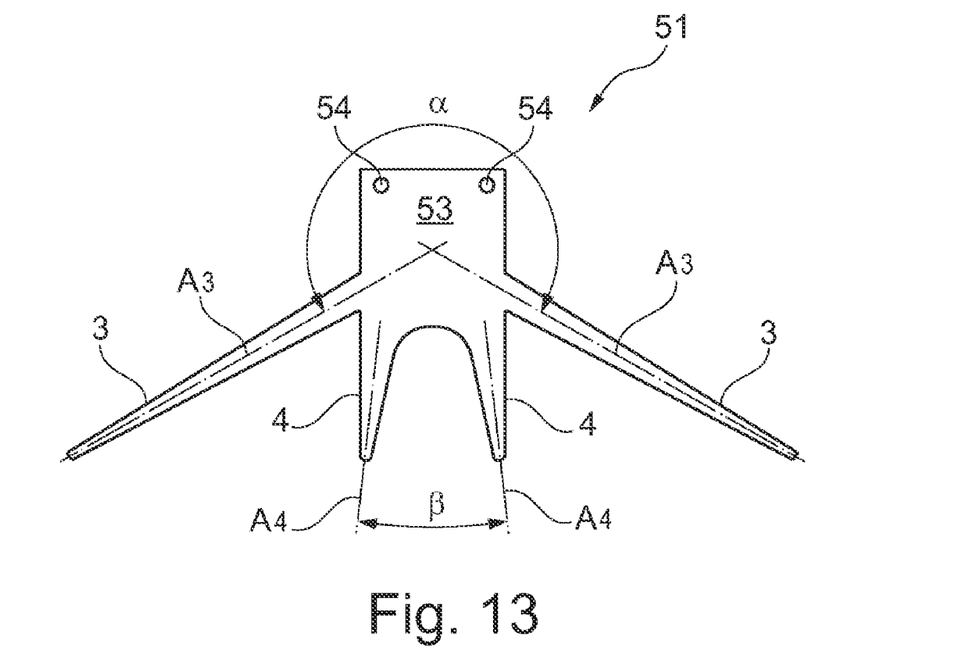
FIGS. 13 and 14 are views analogous to FIG. 1 showing variant embodiments of an implant of the invention.

FIG. 13 shows one such embodiment of an implant 51 of the invention in which the upper suspension stabilizers 3 extend from the sides of the implant body 52 at a distance from its top edge while the two lower stabilizers 4 extend from the bottom corners of the support body 52. This particular configuration defines a kind of upper apron 53 provided with two orifices 54 for passing a separate stabilizing band or for passing posterior stabilizers of an anterior prosthesis used in association with the implant of the invention once the stabilizers of said anterior prosthesis have transfixed the uterosacral ligaments.

Furthermore, in the embodiment shown in FIG. 13, the axes $A_3$ of the upper suspension stabilizers 3 form an angle $\alpha$ that lies more particularly in the range 210° to 260° whereas the axes $A_4$ of the lower suspension stabilizers 4 form an angle $\beta$ of less than 45°, and preferably equal to zero.

Figure 14:
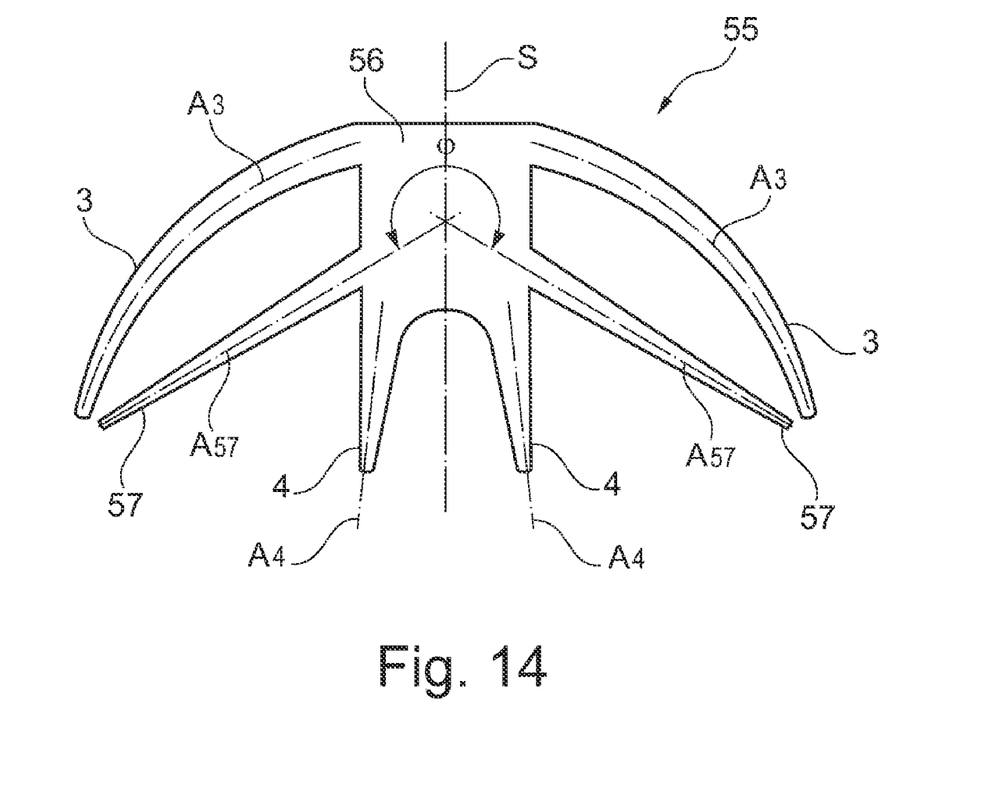

FIG. 14 shows another variant embodiment of an implant 55 for treating prolapse of the vaginal fornix and the rectocele in which all of the suspension stabilizers point downwards. In this variant, the implant body 56 is rectangular in shape. The two upper suspension stabilizers 3 and the two lower suspension stabilizers 4 then extend respectively from the upper and lower corners of the support body 56. In this example, the upper suspension stabilizers 3 are arcuate and their mean fibers $A_3$ which are the equivalent of the axes $A_3$ for a rectilinear stabilizer or arm form an angle $\alpha$ greater than 180°. The angle $\alpha$ is measured between tangents to the mean fibers of the two upper suspension stabilizers. It should be observed that the concave sides of the upper suspension stabilizers 3 face downwards.

In the variant embodiment shown in FIG. 14, the implant 55 also comprises middle suspension stabilizers 57 disposed on either side of the sagittal plane S between the upper and lower stabilizers 3 and 4. The ends of the middle suspension stabilizers point downwards and their axes $A_{57}$ form an angle $\phi$ which is preferably greater than 200° and in more particularly preferred manner lies in the range 210° to 260°. In addition, the ends of the upper and middle stabilizers 3 and 57 situated on the same side of the sagittal plane S converge towards a point or at least extend substantially in the same direction as shown in FIG. 14, with this characteristic making the procedure of implantation easier, as explained below.

The prosthesis as shown in FIG. 14 and as described above is put into place for treating prolapsus of the vaginal fornix and of the rectocele includes anesthetizing the patient and then a stage of dissection. A Muze clamp is then used which applies traction to the cervix of the uterus in order to expose the posterior vaginal fornix. A vaginal incision is made in the posterior face of the cervix transversely on the cervical slope of the vaginal fornix that has been well exposed by the traction.

The edge of the posterior vaginal section is taken hold of in full by three Alis clamps which are pulled downwards so as to expose the rectovaginal plane. Rectovaginal separation is undertaken progressively with eversion of the posterior vaginal wall. This separation is stopped downwards and in the middle of the top of the anal cap. Any dissection of the recto-anal plane is quite pointless or even harmful since this is a plane that is not anatomical but is manifestly created by surgery. The dissection plane should be dissected laterally and in contact with the levator muscle extending upwards through the pubo-coccygeal bundle and then the ilio-coccygeal bundle to reach the level of the coccygeal muscle and the sacrosciatic ligament. This dissection is undertaken with care, pushing back the perirectal fat and the rectum inwards. There is no structure that needs to be sectioned; it suffices to push the perirectal fat inwards while remaining in contact with the muscle floor. The most practical technique is to use a finger, a compress, and above all a set of two narrow and long vaginal valves; these open progressively while monitoring the space visually and without excessive enlargement of the dissected space for sliding a finger.

Figure 15:
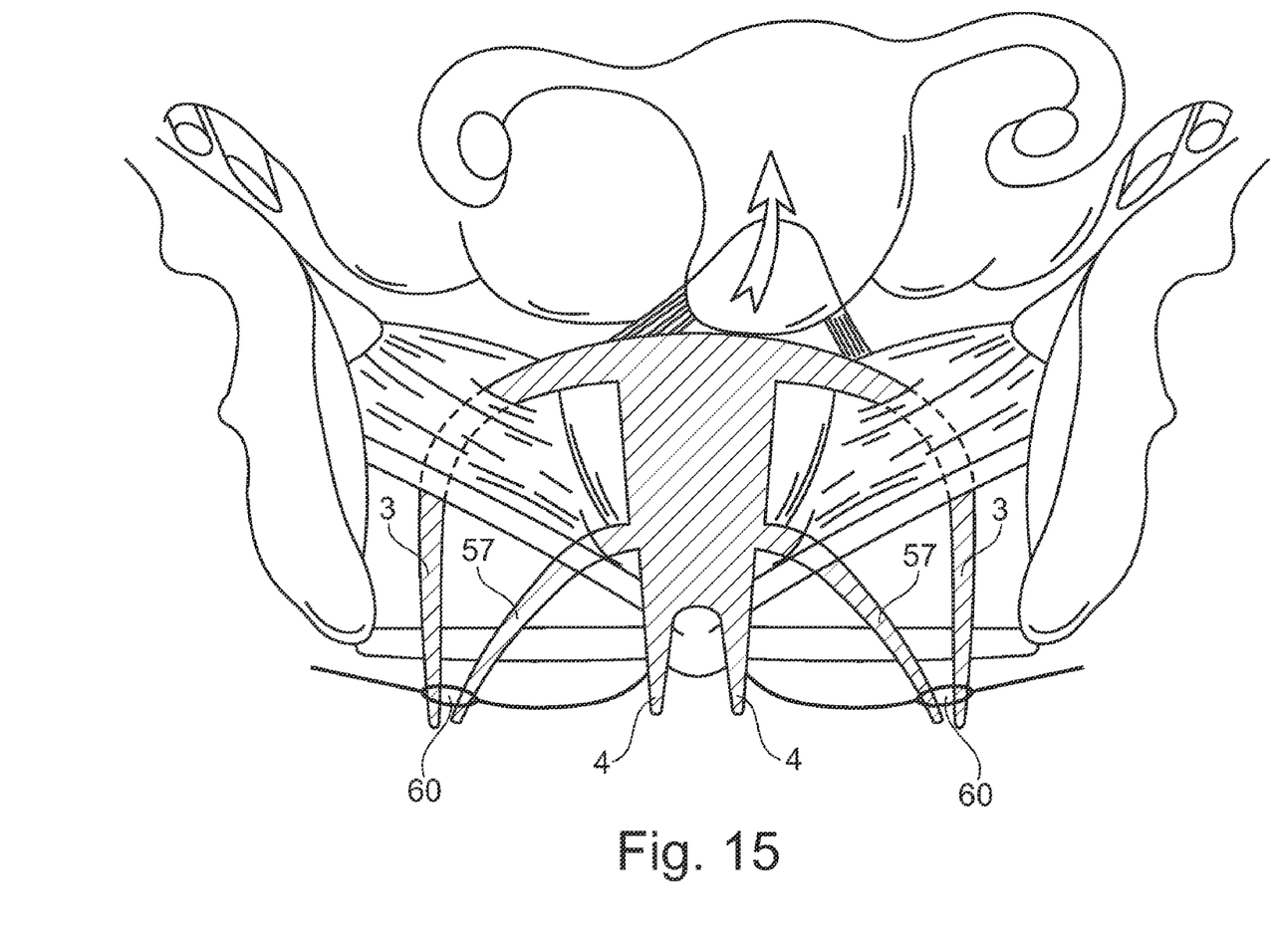
FIG. 15 is an anatomical view showing an example of the FIG. 14 implant being implanted in a woman.

Thereafter, a perforator guide 10 is taken through the buttocks via a point incision 60 situated 15 mm behind the midpoint of the line extending from the anus to the ischion, as shown in FIG. 15. The finger slid into the lateral separation in contact with the sacroiliac ligament receives the tip of the perforator guide 10 and takes it into the posterior vaginal incision, an end of an upper stabilizer 3 of the implant is fixed to the perforator guide 10 and is pulled through the sacrosciatic ligament (sacrosciatic suspension), with the same action being performed on the other side for the other upper stabilizer of the implant 55. The upper edge of the implant is then sutured by two to four stitches to the posterior face of the isthmus and to the uterosacral ligament. The two free ends of the upper stabilizers 3 of the implant are then held in a ready position on a clamp. The middle suspension stabilizers 57 referred to as "pubo-rectal suspension stabilizers" are passed through the pubo-rectal muscles via a transperineal path using the same posterior entry orifice as for the upper suspension stabilizers but with an inward orientation so as to emerge through the pubo-rectal muscle in the middle third of the height of the colpocele. The lower suspension stabilizers, also referred to as "perineal stabilizers", are passed on either side of the vulva fork via a perforator guide 10 that it is more prudent to insert from the inside going outwards (downwards) than upwards, since in that direction the path of the instrument comes close to the rectum and might endanger it.

At the end of surgery, the posterior vaginal incision is sutured with resorbable material and medium traction is exerted on the upper and middle suspension stabilizers in order to raise the vaginal fornix into the proper position, and position the pre-rectal hammock without excessive tension.

The operation is then finished off as described above.

What is claimed is:

1. A system for treating rectocele in a woman, the system comprising:

an implant having an implant shape comprised of a support body from which there extends at least two upper suspension stabilizers each disposed on either side of a sagittal plane on a longitudinal axis, the longitudinal axes forming between them an angle greater than 45°, and two lower suspension stabilizers disposed on either side of the sagittal plane; and an introduction device for inserting the implant in the woman, the introduction device shaped as that of the implant shape and comprising a hollow body defining a cavity that is sized to receive the support body of the implant, tubular straps extending from the hollow body with each defining a cavity for receiving one of the suspension stabilizers of the implant, means for traction extending from an end of each of the tubular straps, and a cut initiator provided on the hollow body.

2. The system of claim 1, wherein the traction means comprises a semirigid needle for each tubular strap.

3. The system of claim 1, wherein the cut initiator comprises at least one opening for passing a cutting instrument.

4. The system of claim 1, wherein the implant is disposed in the cavity of the hollow body and in the tubular straps.

5. The system of claim 4, wherein the implant is loose inside the introduction device.

6. The system of claim 1, further comprising an elongate perforator guide having one end for insertion into the body of the patient and having an opposite end provided with a handle.

7. The system of claim 6, wherein the perforator guide comprises an arcuate portion.

8. The system of claim 7, wherein the arcuate portion of the perforator guide extends over an angular sector in a range of approximately 150° to 170°.

9. The system of claim 7, wherein the arcuate portion of the perforator guide comprises a radius of curvature lying in a range of approximately 30 mm to 60 mm.

10. The system of claim 6, wherein a distal end of the perforator guide comprises a helical shape.

11. The system of claim 10, wherein the helical shape comprises an angle in a range of 180° to 360°.

12. The system of claim 11, wherein the helical shape comprises a radius of curvature lying in a range of 20 mm to 40 mm, with a pitch lying in a range 15 mm to 25 mm.

13. The system of claim 6, further comprising a removable tubular sleeve of a same shape as that of the perforator guide and so configured to be engaged on the perforator guide and to remain within the body of the patient after the perforator guide has been removed so as to define a tunnel for passing the means for traction of an introducer.

* * * * *